(12) United States Patent
Pankratz

(10) Patent No.: US 9,937,028 B2
(45) Date of Patent: Apr. 10, 2018

(54) MUSCLE WALL DEFECT PROSTHESIS AND DEPLOYMENT SYSTEM

(71) Applicant: Bard Shannon Limited, Humacao, PR (US)

(72) Inventor: Stephen Werner Pankratz, Oakville, CA (US)

(73) Assignee: Bard Shannon Limited, Humacao, PR (US)

( * ) Notice: Subject to any disclaimer, the term of this patent is extended or adjusted under 35 U.S.C. 154(b) by 277 days.

(21) Appl. No.: 14/167,379

(22) Filed: Jan. 29, 2014

(65) Prior Publication Data
US 2014/0316444 A1  Oct. 23, 2014

Related U.S. Application Data

(60) Provisional application No. 61/849,532, filed on Jan. 29, 2013.

(51) Int. Cl.
| | |
|---|---|
| A61B 17/08 | (2006.01) |
| A61F 2/00 | (2006.01) |
| A61L 31/04 | (2006.01) |
| A61L 31/06 | (2006.01) |

(52) U.S. Cl.
CPC .......... *A61F 2/0063* (2013.01); *A61L 31/048* (2013.01); *A61L 31/06* (2013.01); *A61F 2002/0072* (2013.01); *A61F 2230/0006* (2013.01)

(58) Field of Classification Search
CPC ...... A61F 2002/0072; A61F 2230/0006; A61F 2/0063
See application file for complete search history.

(56) References Cited

U.S. PATENT DOCUMENTS

| | | | |
|---|---|---|---|
| 5,258,000 A | 11/1993 | Gianturco | |
| 5,366,460 A | 11/1994 | Eberbach | |
| 5,370,650 A | 12/1994 | Tovey et al. | |
| 5,634,931 A | 6/1997 | Kugel | |
| 5,769,864 A | 6/1998 | Kugel | |
| 5,916,225 A | 6/1999 | Kugel | |
| 6,132,470 A * | 10/2000 | Berman | A61L 27/16 623/23.15 |

(Continued)

FOREIGN PATENT DOCUMENTS

| | | |
|---|---|---|
| EP | 1336391 A1 | 8/2003 |
| EP | 1336391 B1 | 12/2011 |

(Continued)

OTHER PUBLICATIONS

Vanos, Robilyn; International Search Report from corresponding PCT Applicaiton No. PCT/CA2014/050057; search completed on Apr. 29, 2014.

(Continued)

*Primary Examiner* — Gregory Anderson
(74) *Attorney, Agent, or Firm* — Wolf, Greenfield & Sacks, P.C.

(57) ABSTRACT

A delivery device for inserting a prosthesis to repair a muscle wall defect has platen and a handle attached to the platen. The platen is collapsible to a reduced configuration. A prosthesis is formed with a pocket to receive the platen and can be maneuvered in to position with the handle. After the prosthesis is secured, the platen is removed.

30 Claims, 12 Drawing Sheets

(56) References Cited

U.S. PATENT DOCUMENTS

| | | |
|---|---|---|
| 6,171,318 B1 | 1/2001 | Kugel et al. |
| 6,174,320 B1 | 1/2001 | Kugel et al. |
| 6,290,705 B1 | 9/2001 | Chan et al. |
| 6,290,708 B1 | 9/2001 | Kugel et al. |
| 6,551,356 B2 | 4/2003 | Rousseau |
| 6,575,988 B2 | 6/2003 | Rousseau |
| 6,669,735 B1 | 12/2003 | Pelissier |
| 6,790,213 B2 | 9/2004 | Cherok et al. |
| 6,800,082 B2 | 10/2004 | Rousseau |
| 6,814,743 B2 | 11/2004 | Chin et al. |
| 7,101,381 B2 | 9/2006 | Ford et al. |
| 7,544,203 B2 | 6/2009 | Chin et al. |
| 7,785,334 B2 | 8/2010 | Ford et al. |
| 7,824,420 B2 | 11/2010 | Eldridge et al. |
| 7,947,062 B2 | 5/2011 | Chin et al. |
| 7,963,942 B2 | 6/2011 | Chen |
| 8,753,358 B2 | 6/2014 | Cook |
| 8,808,315 B2 | 8/2014 | Bailly et al. |
| 8,920,370 B2 | 12/2014 | Sholev et al. |
| 8,945,235 B2 | 2/2015 | Horton et al. |
| 2001/0016754 A1 | 8/2001 | Adams et al. |
| 2004/0019360 A1 | 1/2004 | Farnsworth et al. |
| 2004/0073257 A1 | 4/2004 | Spitz |
| 2004/0087980 A1 | 5/2004 | Ford et al. |
| 2005/0043716 A1 | 2/2005 | Frimer |
| 2007/0299538 A1 | 12/2007 | Roeber |
| 2008/0147200 A1 | 6/2008 | Rousseau et al. |
| 2008/0237287 A1 | 10/2008 | Mitchinson |
| 2009/0082792 A1 | 3/2009 | Koyfman et al. |
| 2009/0270999 A1 | 10/2009 | Brown |
| 2009/0326676 A1 | 12/2009 | Dupic et al. |
| 2010/0069930 A1 | 3/2010 | Mitchell et al. |
| 2010/0241145 A1 | 9/2010 | Cook |
| 2011/0040311 A1 | 2/2011 | Levin et al. |
| 2011/0054500 A1 | 3/2011 | Levin et al. |
| 2011/0082479 A1 | 4/2011 | Friedlander |
| 2011/0144667 A1 | 6/2011 | Horton et al. |
| 2011/0224704 A1 | 9/2011 | Bailly et al. |
| 2011/0295283 A1 | 12/2011 | Darois et al. |
| 2013/0103058 A1 | 4/2013 | Gobran |
| 2013/0178876 A1 | 7/2013 | Horton et al. |
| 2013/0317527 A1 | 11/2013 | Jacinto et al. |
| 2014/0025093 A1 | 1/2014 | Horton et al. |
| 2014/0051915 A1 | 2/2014 | Sholev et al. |
| 2014/0088619 A1 | 3/2014 | Cardinale et al. |
| 2014/0316444 A1 | 10/2014 | Pankratz |
| 2015/0148824 A1 | 5/2015 | Horton et al. |
| 2015/0257866 A1 | 9/2015 | Filipiak et al. |

FOREIGN PATENT DOCUMENTS

| | | |
|---|---|---|
| EP | 2543339 A1 | 1/2013 |
| WO | WO 2011/043795 A1 | 4/2011 |
| WO | WO 2011/128903 A2 | 10/2011 |
| WO | 2013148839 A1 | 10/2013 |
| WO | WO 2014/117270 A1 | 8/2014 |
| WO | WO 2015/104014 A1 | 7/2015 |

OTHER PUBLICATIONS

International Preliminary Report on Patentability for Application No. PCT/CA2014/050057 dated Aug. 4, 2015.

International Search Report and Written Opinion for Application No. PCT/US2015/063386 dated Mar. 18, 2016.

Extended European Search Report for Application No. 14746593.4 dated Jul. 12, 2016.

* cited by examiner

# MUSCLE WALL DEFECT PROSTHESIS AND DEPLOYMENT SYSTEM

CROSS-REFERENCE TO RELATED APPLICATIONS

The present application claims priority from U.S. Provisional Application No. 61/849,532 filed Jan. 29, 2013; the entire contents of which is incorporated herein by reference.

FIELD OF THE INVENTION

This invention relates to apparatus and a method for facilitating the repair of hernias and muscle wall defects. It relates more particularly to a system that aids in the positioning and fixation of a prosthesis over the muscle wall defect.

BACKGROUND OF THE INVENTION

One method of repairing a muscle wall defect or hernia of a patient's abdominal wall muscle is to insert a prosthetic material or mesh through the defect and so as to be inside the patient's muscle wall. The prosthesis, which is generally larger than the defect, is then positioned in a planar orientation relative to the muscle wall, covering the defect in its entirety. The prosthesis is then typically fixed to the underside side of the muscle wall or tissue surrounding the defect, with the use of fixation tools such as sutures and/or tackers.

A second method of repairing a hernia is to place the prosthetic material or mesh through the muscle wall defect, and position it in a planar orientation between the muscle wall and the posterior sheath.

Prosthetic devices have recently been developed that aid in the orientation, positioning and fixation of the prosthesis to the underside of the muscle wall defect. These devices generally consist of (a) a prosthesis or base that may be folded and placed through the defect; (b) a support member or washer that is combined with the prosthesis and that urges the prostheses into a planar orientation after it has been placed through the defect; and (c) a handle or positioning straps that can extend through the defect and can be used to hold the prostheses close to or against the muscle wall while the prosthesis is sutured or tacked to the abdominal wall. At least a portion of positioning straps are subsequently cut off once the prosthesis is fixed in place, allowing tissue anterior to prosthesis and muscle wall to be sutured closed.

U.S. Pat. No. 7,101,381 describes a prosthesis comprising a resilient support member disposed on a patch, the resilient support member being constructed and arranged to urge the patch into a planar configuration. This additional support member, attached to the layers of the prosthesis, however, is permanently implanted in the patient and introduces additional stiffness or rigidity, which may interfere with the prosthetics ability to conform to the contours of the patient's abdominal wall. This arrangement makes it more difficult to ensure that the patch remains flat against patients' moving and contoured abdominal wall. The flat and tight junction between the patch and the patients' abdominal wall is necessary for ensuring that intra-abdominal tissue or bowels cannot become wedged between the prosthetic and the abdominal wall, causing a hernia recurrence (particularly for the first method of repairing a hernia described above).

U.S. patent US2011/0144667 attempts to resolve the high degree of stiffness that results from this support member by describing a support washer that is not attached or sutured to the base of the prosthetic, but is instead, free-floating. This washer of this device is still, however, contained within the enclosed layers of the prosthesis, and permanently implanted with the prosthesis. While this prosthesis may reduce some of the stiffness when compared to the support member described in U.S. Pat. No. 7,101,381, the reduced stiffness also compromises the ability of the support washer to urge the prosthesis into a planar configuration. Because surgeons must ensure that this prosthesis is in a planar configuration and the prosthesis completely covers the muscle wall defect, many find this device difficult to use.

Both the additional support member described in U.S. Pat. No. 7,101,381, and the free-floating support washer described in US2011/0144667 introduce additional foreign body material that is implanted into the patient. This additional foreign body material not only itself adds rigidity to the abdominal wall, it further compromises the flexibility and physiologic function of the abdominal wall by eliciting a foreign body response that results in a stiffer and weaker muscle repair around the prosthetic.

One familiar with the art will recognize the importance of fixing the patch, particularly the peripheral edge of the patch, to the abdominal wall. This facilitates a tight junction between the patch and the muscle wall, and facilitates integration of the patch to the abdominal wall over time. Underlying tissue or organs cannot then become wedged between the patch and the abdominal wall, which could otherwise lead to an incomplete repair, a hernia recurrence, or other post-operative complication.

U.S. Pat. No. 7,101,381 goes on to describe a patch that has an access opening that is adapted to provide entry into the inferior of the pocket (between the layers) to facilitate the positioning of the patch over the tissue or muscle wall defect. This pocket may also be accessed by sutures or a tacker in order to fix the patch to the abdominal wall. However, once the patch has been positioned relatively deeply within the abdominal wall, it is difficult or even impossible for a surgeon to see the access opening of the patch during fixation. It is thus very challenging for the surgeon to place instrumentation through the muscle wall defect (which is typically smaller than the patch), into the access opening of the patch, and fix the peripheral edge of the patch to the underside of the abdominal wall, without unintentionally perforating the patient's organs, tissue or other critical structures.

The resilient support member that U.S. Pat. No. 7,101,381 describes and that urges the patch in the planar configuration is disposed on the patch. This support member, and the stitching that disposes the resilient member onto the patch, become the perimeter of the access opening, and a barrier that prevents access through the access opening or pocket, to the peripheral portion or edge of the patch. It is therefore not possible to suture or tack the peripheral portion of the patch to the abdominal wall from within the access opening of the patch. This can prevent complete integration of the patch to the abdominal wall, and can allow patient tissue or organs to be wedged between the patch and the abdominal wall.

It is an object of the present invention to obviate or mitigate the above disadvantages.

SUMMARY OF THE INVENTION

The present invention relates to a device and method for implanting prosthesis used to overlie a hernia or abdominal wall defect, and that aids in the orientation, positioning and fixation of the prosthesis to the abdominal wall while limiting the amount of foreign body material implanted in the patient.

The hernia or soft tissue or muscle repair device and methods described here utilize a system comprising, in combination, a biologically compatible implantable prosthesis or patch, and a delivery device for delivering the prosthesis to the repair site. The biologically compatible implantable prosthesis or patch is comprised of a first layer of material that covers the muscle wall defect. A second layer or rim of material is attached to the first layer at the peripheral edges of each layer, and provides an opening in the form of a hole or slit that allows access to an inner space or pocket formed between the first and second layers.

Both layers of the prosthesis must be comprised of biocompatible material(s), flexible enough to conform to patients' abdominal wall, and must cover patient's muscle wall defect. Synthetic materials may be used, and are intended to provide permanent coverage of the muscle wall defect and reinforcement to prevent future hernia recurrences. These materials include, but are not limited to, polypropylene, polyethylene, polyethylene terephthalate and/or expanded polytetrafluoroethylene, and may be knitted or woven together, and arranged in flexible planar sheets. Examples of such materials include Atrium Medical's ProLite and ProLite Ultra polypropylene hernia mesh, Ethicon's Prolene polypropylene hernia mesh, Bard's Marlex polypropylene hernia mesh and Ethicon's Mersilene mesh constructed from polyethylene terephthalate. These synthetic materials may also be co-knitted with bioabsorbable materials such as polyglycolic acid. The synthetic or synthetic-bioabsorbable knitted material may also be coated on the side that will face the viscera, with a material or combinations of materials that reduce or prevents the adhesions of bowels or other tissue. Examples of these materials include, but are not limited to cross-linked omega-3 fatty acid oil; combinations of sodium hyaluronate, carboxymethylcellulose and polyethylene glycol; oxidized regenerated cellulose; collagen oxidized films; and combinations of monocryl and polydioxanone film. Currently available devices that aid in the positioning and fixation of a prosthesis over the muscle wall defect, and that utilized a prosthesis constructed from combinations of polypropylene and bioabsorable coatings include Atrium Medical's VPatch™ (which utilizes cross-linked omega-3-fatty acid oil coated polypropylene) and C.R. Bard's Ventrelex ST (which utilizes a combination of sodium hyaluronate, carboxymethylcellulose and polyethylene glycol; and polypropylene).

Alternatively, the prosthesis can be comprised of a collagen matrix, sourced from human tissue (allografts), or animal tissue (xenografts). These materials provide a collagen framework that may be repopulated with the patient's own cells and tissue after implantation and overtime. These sources are typically used when synthetic sources are not recommended, and often used during the repair of infected or contaminated hernia defects. Examples of currently available collagen matrix materials include TEI Bioscience's SurgiMend which is a xenograft sourced from fetal bovine, LifeCell's Alloderm allograft sourced from human cadavers, and LifeCell's Strattice xenograft sourced from porcine.

For delivering the prosthesis, there is also provided a separate delivery device, which is comprised of a flexible and planar support piece, and optionally a handle. The support piece is comprised of a material with elastic and/or flexible properties, that will fold or temporarily collapse from its free body planar configuration. Before use, the support piece of the delivery device is placed or "nested" within the pocket between two layers of the prosthesis. Once positioned in the pocket, the support piece may be released, allowing it to expand back into its natural planar orientation between the two layers of the prosthesis. The support piece of the delivery device is constructed from a material with an inherent rigidity that provides a bias toward a flat or planar orientation yet is sufficiently pliable to allow its deformation during placement at the repair site. Useful materials include, but are not limited to polymeric material such as polypropylene, polyethylene terephthalate, polyethylene, silicone, nitinol and/or polytetrafluoroethylene.

The handle of the delivery device can be in the form of a tether, strap or extension, and may be used to aid in the positioning of the support piece while it is nested in the prosthesis. Because the handle is not attached to the prosthesis, but rather attached to or contiguous with the support piece, the handle may also to be used to remove the removable piece from the prosthesis and out of the defect after the prosthesis has beets fixed in place. The handle is constructed of a flexible material that is long enough to extend though the muscle wall defect and surrounding tissue, while being held or handled outside of the defect by the surgeon. It must also be durable enough to withstand the force exerted on it by the surgeon while pulling on it and positioning the removable piece relative to the defect, or removing the removable piece from the prosthesis and out of the muscle wall defect. Some examples of materials that the handle may be constructed from include, but are not limited to polypropylene, polyethylene terephthalate and/or polytetrafluoroethylene.

When the support piece is nested in the prosthesis, the two pieces can then be folded or collapsed as one piece while placed through the muscle wall defect. Once placed through the defect, the delivery device can be allowed to return to its natural, planar shape. This urges the prosthesis, constructed from a material that is typically flexible or flimsy, into a planar orientation relative to the abdominal wall. The handle that is fixed to, or contiguous with the support piece, can be then be used to position the prosthesis relative to the defect. The prosthesis can then be fixed to the abdominal wall muscle or tissue surrounding the defect by using, as an example, sutures and/or a tacker. The support piece of the delivery device is constructed preferably from a material that is difficult to penetrate with fixation tools, and may be used to prevent the suture needles or tacks from unintentionally penetrating underlying organs or tissue during fixation of the prosthesis to the abdominal wall. Then, the support piece can be forced to fold or collapse, and retracted and removed from the prosthesis (or base) through the muscle wall defect by pulling on the removable portion of the delivery device, or on the available handle. This allows for a convenient repair of the muscle wall defect while leaving only the prosthesis implanted. Because no support members or washers are left behind, the prosthesis can better conform to the moving contours of the patient's abdominal wall. There is also less foreign body material implanted in the patient, leading to a better, more flexible muscle wall defect repair.

In one embodiment, the space or pocket created between the first layer and second layer or rim of the prosthesis may be accessed so that the second layer that extends about the rim of the first piece may be positioned and fixed to the muscle wall. This pocket is not interrupted by any support member, washer, or stitching that disposes a support member or washer onto the patch. Thus, the pocket may extend all the way to the periphery of the prosthesis, making it possible to suture or tack the peripheral edge of the patch to the abdominal wall, from within the pocket of the patch.

In one exemplary embodiment of the present invention, the second layer of the implantable prosthesis may contain at least one centrally located opening thus creating a peripheral rim of material against the first layer. The space or pocket between the rim and the first layer may be accessed through the hole so that the rim of material may be positioned and fixed to the muscle wall.

In accordance with another example embodiment of the present invention, the first layer of the implantable prosthesis may be, at least at portions of the peripheral edge, folded over, creating the second layer or rim or partial rim of material. The space between the rim or partial rim, and the first layer may be accessed so that the rim of material may be positioned and fixed to the muscle wall.

In accordance with yet another example embodiment of the present invention, the second layer of the prosthetic may contain a slit extending across at least a portion of the second layer, allowing access to the space between the first and second layers, so that the second layer of material may be positioned and fixed to the muscle wall.

In one embodiment, the implantable prosthesis may be at least in part constructed using a material that includes a plurality of interstices that are constructed and arranged to allow tissue in-growth into the abdominal wall. This material may include, but is not limited to polyethylene or polyester. This material may also be coated with an absorbable substance that reduces the formation of undesirable adhesions of tissue or organs to the implantable prosthesis.

In yet another embodiment, the implantable prosthesis is at least partially comprised of a biological material including but not limited to porcine, fetal porcine, bovine, fetal bovine, or equine dermis.

In one embodiment, at least a portion of the implantable prosthesis that faces and is placed against the muscle wall and muscle wall defect is susceptible to the formation of adhesions with tissue.

In accordance with further aspects of the present invention, the delivery device may consist of, but is not limited to polypropylene, polyethylene, silicone, nitinol or other types of plastic and/or metal materials.

In another embodiment, the delivery device contains a slit or fold or region of increased flexibility, allowing the delivery device to be more easily folded or collapsed from its natural configuration, and fit into or removed from the implantable prosthesis.

In one embodiment, the delivery device includes a handle in the form of a tether(s), strap(s) or extension(s) can extend through the tissue or muscle wall defect when the implantable prosthesis and delivery device are positioned over the detect, for use in positioning the removable piece and the prosthesis, and for use in removing the prosthesis when properly positioned and fixed.

In accordance with further aspects of this invention, the delivery device consists of an outer peripheral edge and an inner region within the outer peripheral edge; the tether(s), strap(s), or extension(s) may extend from the inner region.

In another embodiment, a handle may be attached to the delivery device in a position that is diametrically opposing a slit in the delivery device. Pulling on the handle, particularly in a direction that is obtuse to the direction of the silt, forces the delivery device against the mesh and/or muscle wall, urging the two sides of the slits to overlap each other, and urging the positioning device into a collapsed conformation. This urges the positioning device into its collapsed conformation and allows it to be readily removed from the implantable prosthesis and out of the muscle wall defect.

In another embodiment, a method is provided for the repair of a hernia or soft tissue defect uses a biologically compatible implantable prosthesis or patch, comprised of a first layer of material that covers the muscle wall defect. A second layer or rim of material that is attached to the first layer at the peripheral edge contains an opening in the form of a hold or slit, enabling access to an inner space or pocket between the first and second layers. A separate delivery device, which is comprised of a flexible and planar support piece, and optionally a handle, is used to position, fix the prosthesis to the abdominal wall. The support piece is comprised of an elastic material, is folded or temporarily collapsed from its natural planar configuration and placed or nested in the pocket between two layers of the implantable prosthesis. Once positioned in the pocket, the delivery device may be released, allowing it to expand back into its natural planar orientation between the two layers of the prosthesis. Now combined, the prosthesis and the support piece can then be folded or collapsed as one piece while placed through the muscle wall defect. Once in place relative to the defect, the delivery device is allowed to return to its natural, planar shape, also urging the prosthesis into a planar orientation relative to the abdominal wall. The handle, in the form of at least one tether, strap, or extension that is fixed to or contiguous with the support piece, can be used to position the combined support piece and implantable prosthesis relative to the defect. The prosthesis can then be fixed to the abdominal wall muscle or tissue surrounding the defect by using, as an example, sutures or a tacker. During fixation, the planar removable piece of delivery device may be used to prevent the suture needles or tacks from unintentionally penetrating underlying organs or tissue. Then, the removable piece can be forced to fold or collapse, removed or retracted from the prosthesis, and pulled through the muscle wall defect by pulling on the handle.

BRIEF DESCRIPTION OF THE DRAWINGS

Embodiments of the invention will now be described by way of example only with reference to the accompanying figures. These embodiments are further explained in the detailed description that follows.

FIG. 11 illustrates in a top perspective view, an alternative embodiment of a prosthesis;

DETAILED DESCRIPTION OF THE INVENTION AND PREFERRED EMBODIMENTS

The present invention is a device that aids in the deployment, positioning and fixation of a prosthesis to an abdominal wall to repair a defect while limiting the amount of foreign body material implanted in the patient. Muscle wall defects can include, but are not limited to, umbilical hernias, epigastric hernias, incisional or other ventral hernias, inguinal hernias, femoral hernias, and muscle wall defects or holes left in the abdominal wall front trocars used for laparoscopic surgery. Described herein are only a few exemplary embodiments. One familiar with the art will recognize that parameters, including size and shape of the components of this invention, as well as the types of materials used for the components, may be altered to accommodate different types and/or sizes of abdominal wall defects while staying within the scope of the invention described herein.

Figure 2:
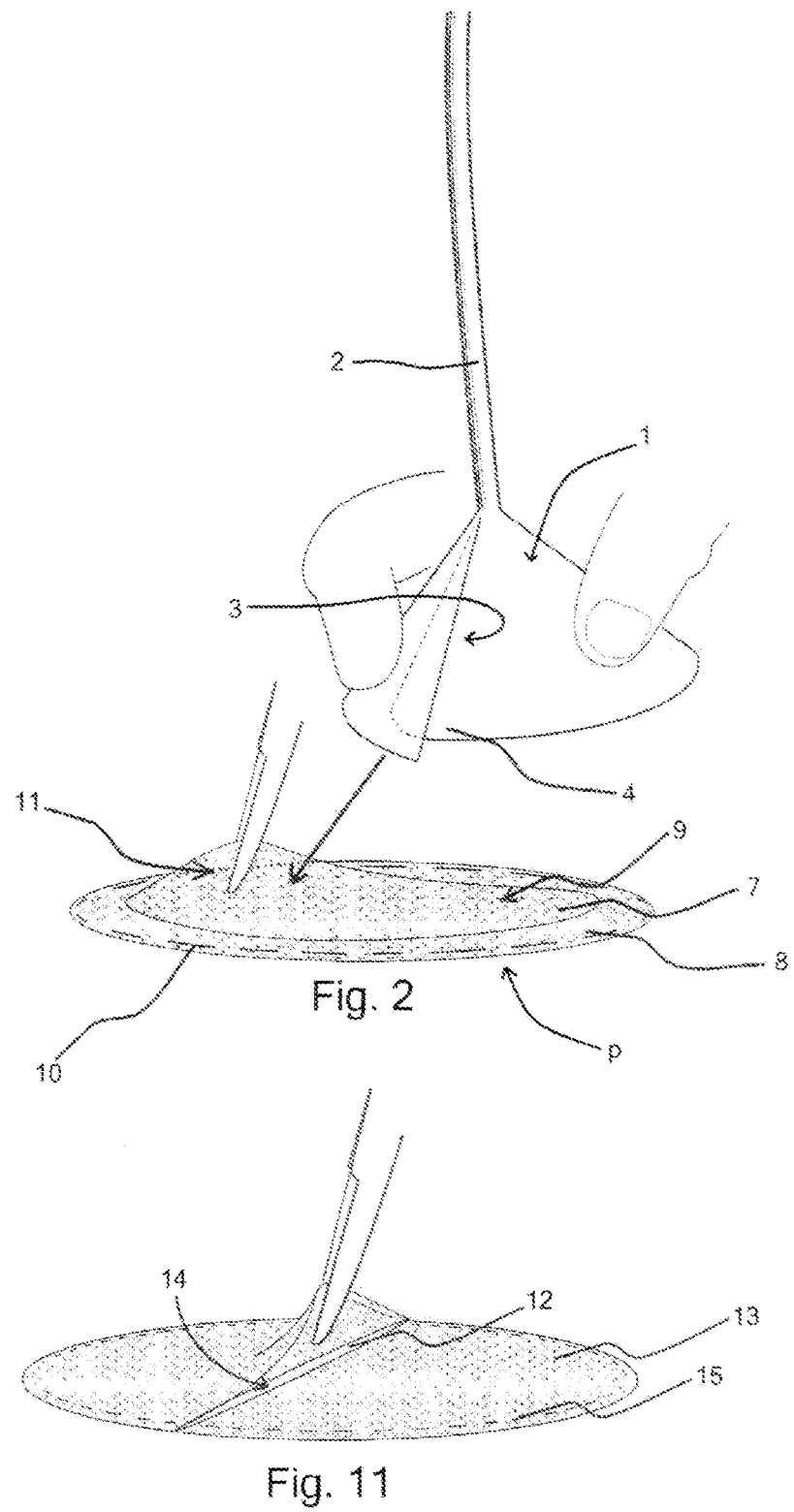
FIG. 2 illustrates in a top perspective view, the delivery device of FIG. 1, being collapsed by the user prior to being inserted into the prosthesis.

FIG. 2 depicts an implantable prosthesis P, which consists of at least two juxtaposed layers, 7 and 8. Layers 7 and 8 are each constructed using a biologically compatible material. The material is flexible and includes a plurality of interstices that are arranged to allow tissue in-growth and integration into the abdominal wall. Suitable materials include polypropylene, polyester, polytetrafluoroethylene (PTFE) and expanded polytetrafluoroethylene (ePTFE). As a further preference the material used for the layers 7, 8, is knitted.

The second layer, 8, is formed as an annulus having an opening in the form of a centrally located hole, 9, which creates a peripheral rim of material when placed against the first layer, 7. Layers 7 and 8 are connected at the peripheral edge, such as by stitching, 10, creating an enclosed accessible space or pocket, 11. In one example embodiment, the side of layer 7 that faces the patients' organs, shown in FIG. 4, as 7a, is covered in a substance that reduces the formation of undesirable adhesions of tissue or organs to the implantable prosthesis. One familiar with the art will recognize that this will be particularly important if the underlying layer, 7, is constructed from a knitted material or one that includes a plurality of interstices that could otherwise allow the formation of unwanted adhesions over time from the underlying organs or tissue.

In an alternative embodiment, layers 7 and 8 are constructed from biological material such as a collagen matrix, typically derived from human or animal tissue. Suitable materials include porcine, fetal porcine, bovine, fetal bovine, equine and human cadaver tissue.

Figure 1:
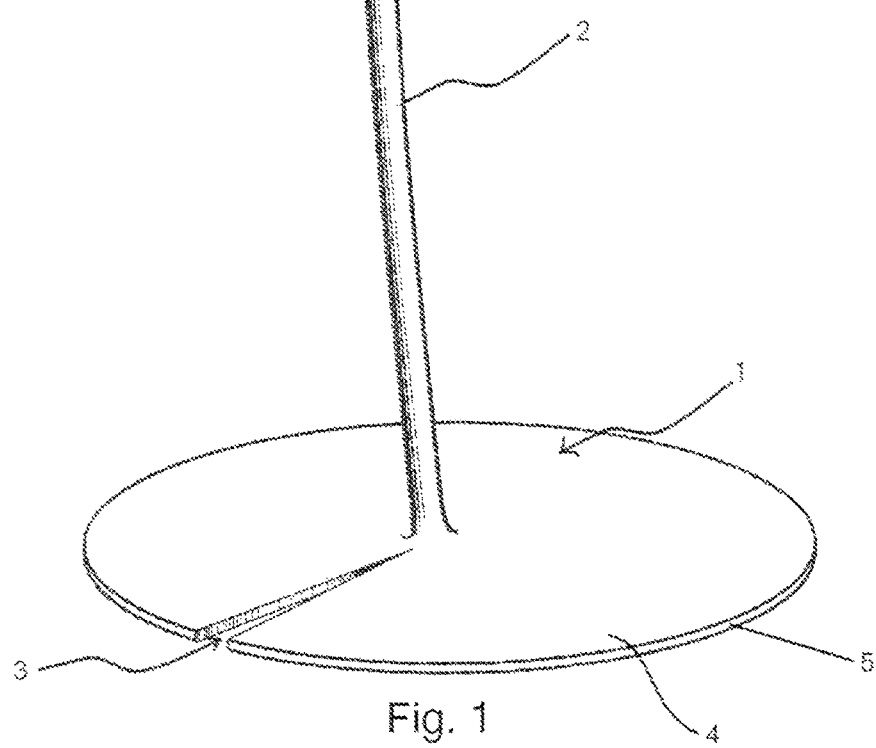
FIG. 1 depicts from a top perspective view, one exemplary embodiment of the delivery device.

Referring now to FIG. 1, a prosthesis delivery device 1, contains a planar support piece or platen, 4, and a handle, 2. The handle 2 is integrally formed with the platen 4 to inhibit separation of the handle 2 and platen, 4. The platen 4 is constructed out of biologically compatible flexible material such as an elastic plastic polymer material, typically one of polypropylene, polyethylene, polyethylene terephthalate, poly(glycolide-co-L-lactide), polydioxanone, and silicone, having flexibility sufficient to adopt a collapsed form allowing the support piece to pass through the opening, 9 of the prosthesis P. To facilitate flexure, the platen 4 has a zone of weakness, which, in the embodiment of FIG. 1, is a radial slit, 3, which extends from adjacent the handle 2 to the outer peripheral edge 5. The slit 3 allows the platen to more readily be folded from its natural or planar configuration, shown in FIG. 1, and into a conical collapsed configurations, shown in FIG. 2. In the planar configuration the edges of the slit 3 substantially abut to present on continuous planar surface and peripheral edge.

As shown in FIG. 1, the handle 2 is flexible but has sufficient rigidity to control movement of the platen and allow manipulation of the platen 4. In the embodiment of FIG. 1, the handle 2 is integrally formed with the platen 4 and extends 2 to 20 cm from the platen, but more preferably 5-15 cm from the platen. The handle 2 may be made from the same material as the platen 4, or from another material where different mechanical characteristics are required. Preferably, the material used for the handle 2 is polypropylene, polyethylene, PTFE and/or silicone, having a width that ranges from 0.5 mm to 20 mm, but more preferably 3-6 mm, and a thickness of 0.5 mm to 2.0 mm but more preferable 0.7-1.2 mm, and having a flex modulus of 125,000 psi to 275,000 psi.

Figure 3:
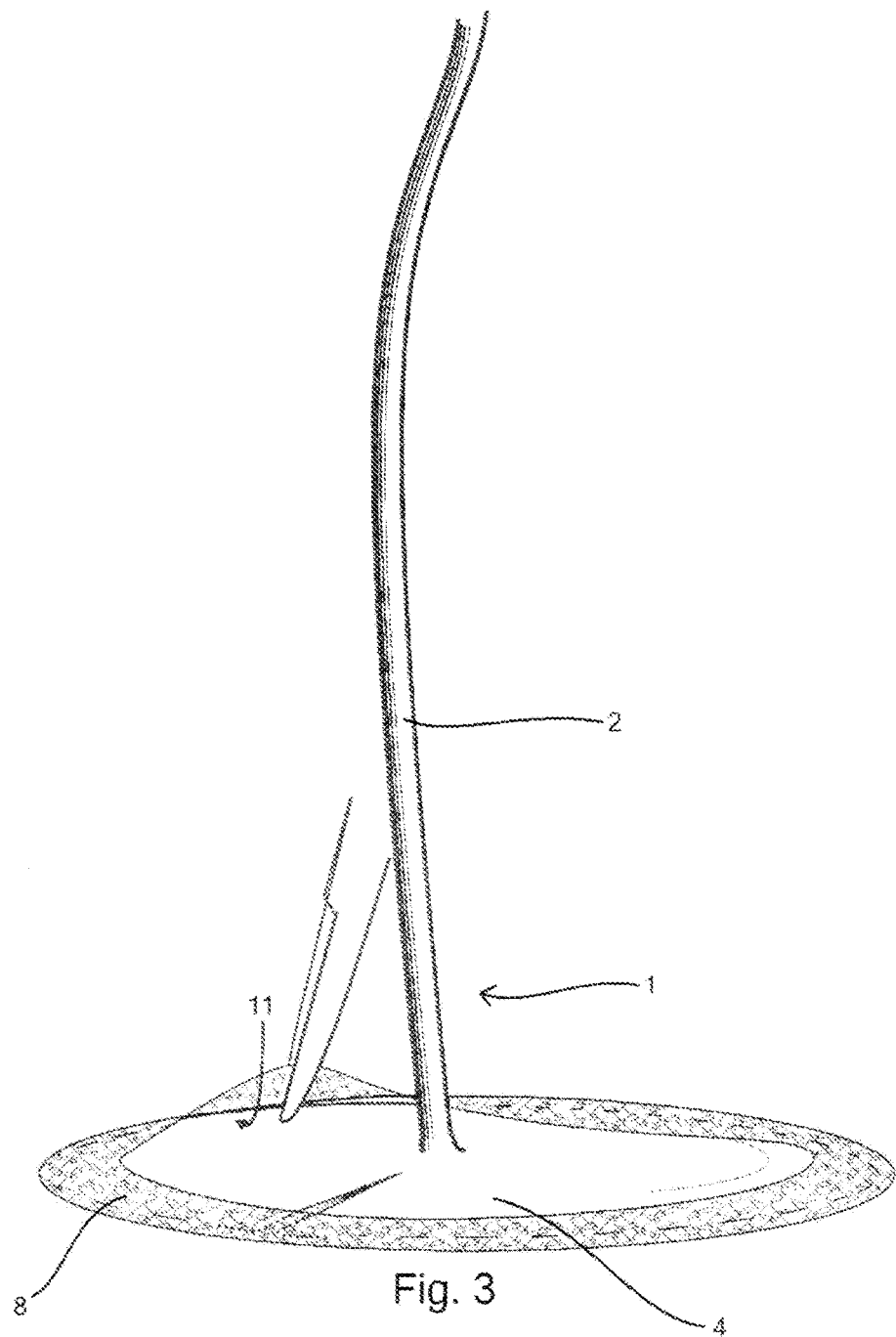
FIG. 3 illustrates in a top perspective view, the delivery device after it has been inserted into the prosthesis.

To assemble the prosthesis P on the delivery device 1, the outer peripheral edge, 5, of the platen 4 is pushed downwardly to form a cone with the slit 3 accommodating the reconfiguration from the free body state. Once the platen 4 has been collapsed to a circumference less than that of opening 9, it may be positioned in the pocket 11 formed between the two layers 7,8 of the prosthesis P. Once positioned, it may be released, allowing it to be restored into its natural planar orientation and nested between layers 7 and 8, as depicted in FIG. 3. With the platen 4 of the delivery device 1 nested between the layers 7, 8 of the prosthesis P, the delivery device 1 and the prosthesis P can be manoeuvred and folded or flexed as a unit.

In order to provide complete coverage of the muscle wall defect, the surgeon will choose a prosthesis with an area that is larger than that of the muscle wall defect. In a repair known as an underlay repair, the prosthesis must be folded or rolled in order to fit it through the muscle wall, behind or posterior to the muscle wall defect. The delivery device 1 and the prosthesis P is packaged and presented to the user or surgeon, separately, or combined as seen in FIG. 3. In either case, it is important that the size of the platen 4 is large enough to fit between layers 7 and 8 without unintentionally or too easily sliding out from between layers and out of the centrally located hole, 9. It is also important that the platen 4 is not too large, and must be able to fit between layers 7 and 8, and within the pocket, 11, and within the boundaries created by the stitching, 10. The thickness, flexibility and/or elasticity of the platen 4 of the delivery device is selected to accommodate the different support requirements of varying sizes of prostheses P.

In one particular embodiment, the platen 4 is formed from a polymer such as polypropylene having a flex modulus from 125,000 to 175,000 psi. The thickness of the polymer used is generally between 0.05 mm to 2.0 mm, but is preferably between 0.1 mm and 1 mm. The diameter of the removable piece will generally be 0.1 mm to 5.0 mm less than the internal diameter of the pocket 11 which is defined by stitching, 10. The diameter of the platen 4 will more specifically be 0.5 mm to 3.0 mm less than the diameter of the pocket 11 which is defined by stitching, 10.

Figure 4:
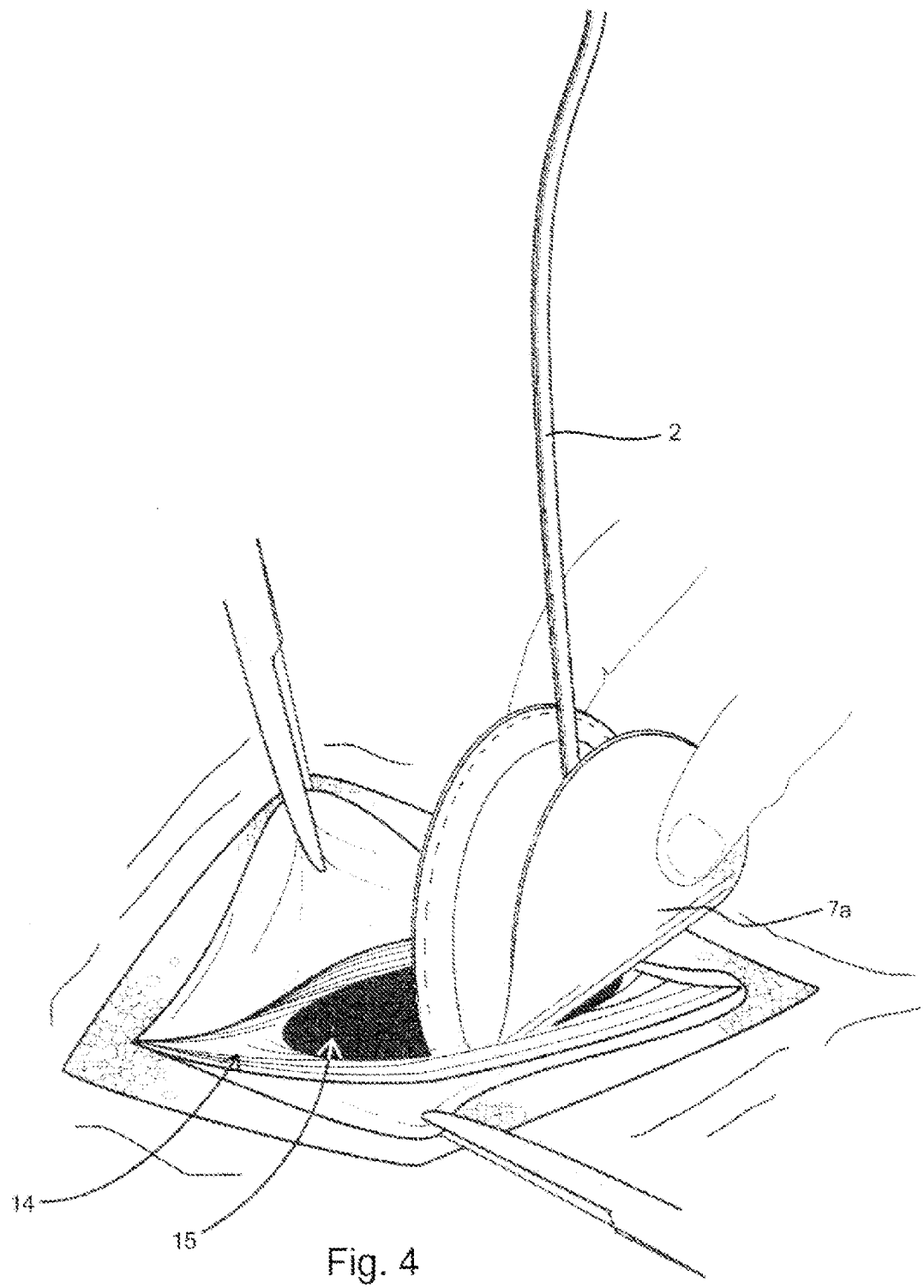
FIG. 4 illustrates in a top perspective view, the initial insertion of the delivery device through the muscle wall defect.

When combined, the platen 4 and the prosthesis P can be rolled or folded by the surgeon, for example in half as seen in FIG. 4, and inserted through the muscle wall detect, 15. Once on the posterior side of the abdominal wall the surgeon can release the combined platen 4, and prosthesis P, allowing the platen 4 to return to its natural planar confirmation due to its elastic nature. The resilience of the platen 4 urges the prosthesis into the planar configuration as well, and provides a temporary support for the prosthesis P as it is positioned in place. This keeps the prosthesis, which is typically constructed from light-weight materials and can be flimsy, in an expanded, planar orientation relative to the abdominal wall. This makes it easier for the surgeon to fix the prosthesis to the posterior side of the abdominal wall surrounding the muscle wall defect, using for example, sutures or tacks.

Figure 5:
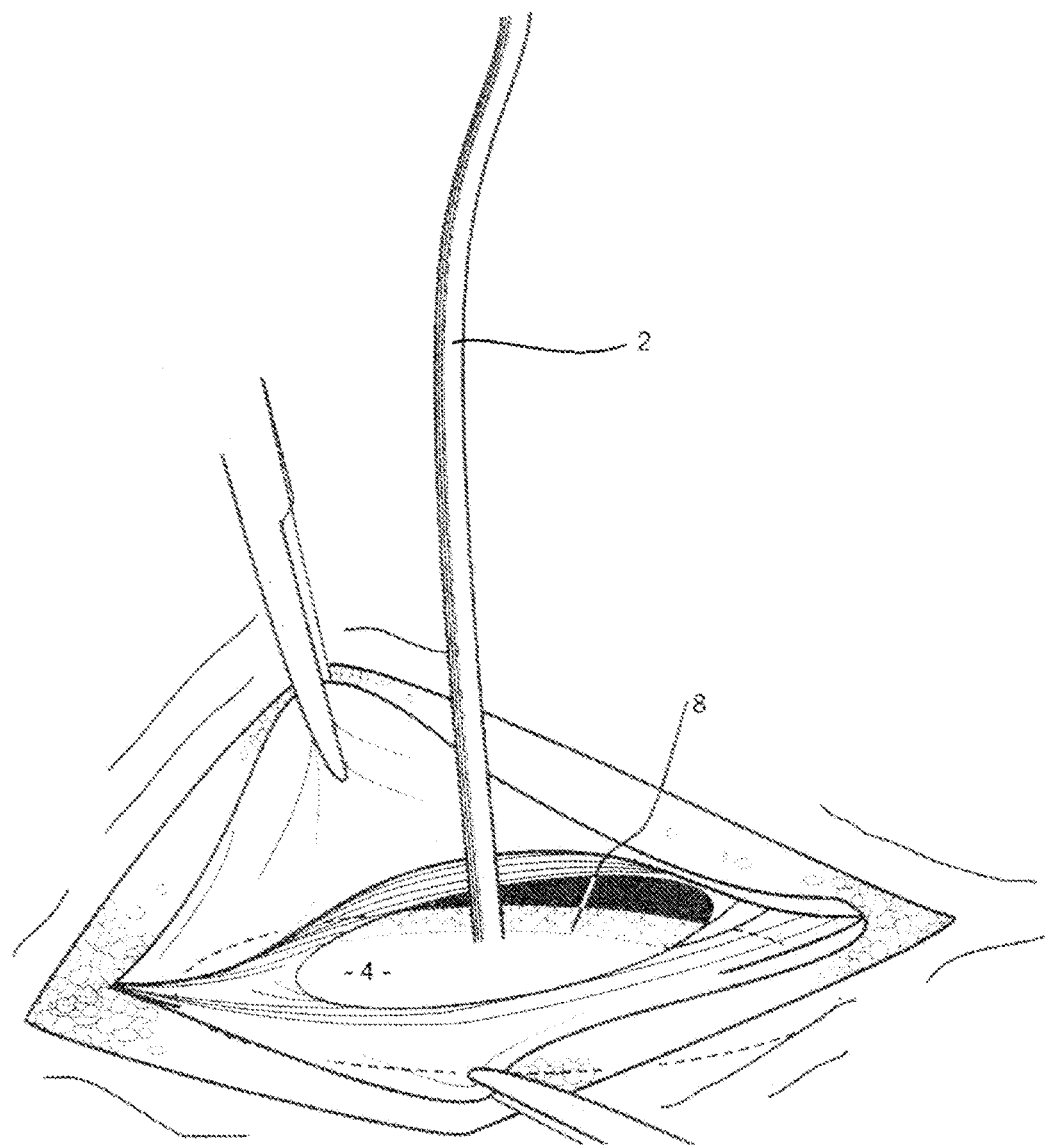
FIG. 5 illustrates in a top perspective view, the delivery device and prosthesis, after they have been inserted through the muscle wall defect.
Figure 6:
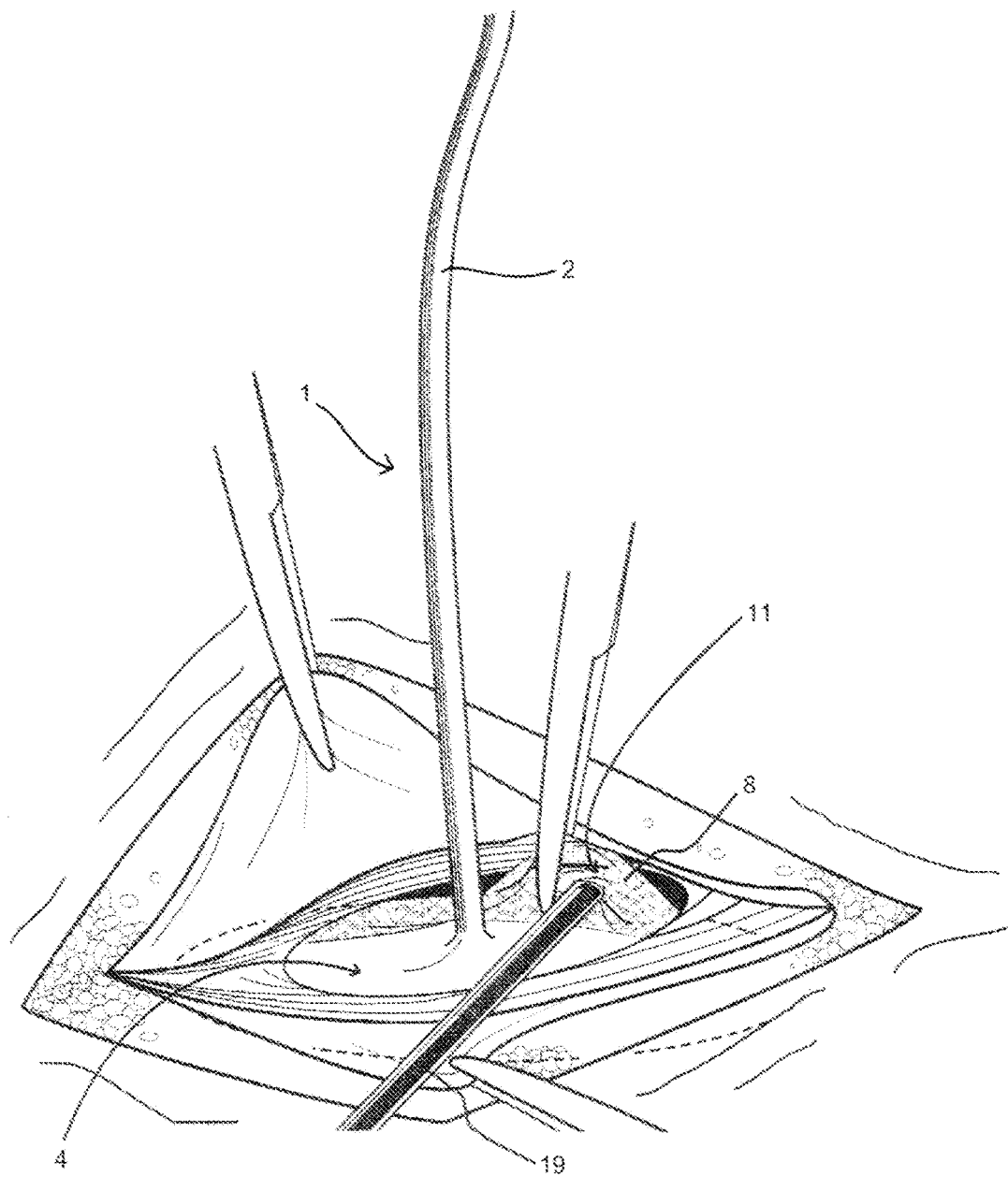
FIG. 6 illustrates in a top perspective view the fixation of the prosthesis to the muscle wall.
Figure 7:
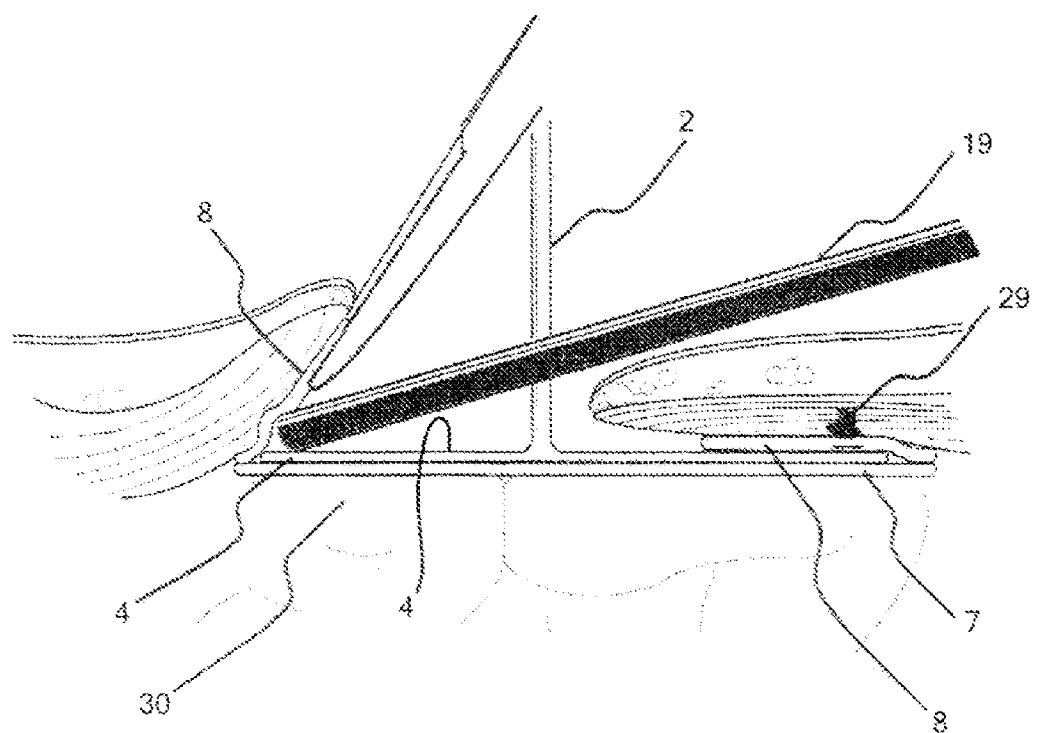
FIG. 7 illustrates in a cross-sectional view, on the line VII-VII of FIG. 6.

The handle 2 is configured to extend through the muscle wall defect so as to be accessible to the surgeon. The handle 2 is used by the surgeon to position and pull the platen 4 of the delivery device 1, along with the prosthesis, up against the muscle wall, as shown in FIG. 5, FIG. 6 and FIG. 7. Once the combined delivery device 1 and prosthesis P are in position relative to the muscle wall defect, the prosthesis is fixed to the underside or posterior side of the muscle wall defect. This may be done by using sutures or by using a tacker, 19 shown in FIG. 6 and FIG. 7. The end of the tacker 19 can, for example, be placed into the pocket 11 between the first and second layers of the prostheses, 7, 8, pushing the second layer of material, 8, upwards against the posterior side of the abdominal wall. A tack deployed from the end of the tacker, 19, can subsequently tack the second layer of material, 8, to the posterior side of the abdominal wall. FIG. 7 shows a tack, 29, that has been deployed, to pass through the second layer of material, 8 to the abdominal wall in this way. Subsequent tacks may be deployed in this fashion, along the entire peripheral edge of the prosthesis P until it is adequately anchored to the abdominal wall, and around the muscle wall defect. During this procedure, the handle 2 is used to ensure close contact between the layer of material 8 and the abdominal wall, whilst being flexible to allow adjustment for access of the tacker 19. Because the platen 4 of the delivery device 1, lies below the tacker, 19, it deflects sutures or tacks that might otherwise unintentionally perforate underlying tissue and organs such as bowel, 30. Once the prosthesis 2 is fully anchored, tissue or organs should not be able to become lodged between the abdominal wall and the prosthesis.

The support provided by the platen 4 avoids the need for a separate support ring in the prosthesis and so allows the tacker 19 to access the prosthesis at the peripheral edge 5. One skilled in the art will recognize that it is important to access and fix the peripheral edge of the prosthesis to the posterior side of the abdominal wall to 1) ensure good apposition and integration of the prosthesis to the abdominal, and to 2) prevent tissue and organs lodging between the prosthesis and the abdominal wall to avoid dislodgment of the mesh and recurrence of the hernia or incomplete repair of the muscle wall defect.

Figure 8:
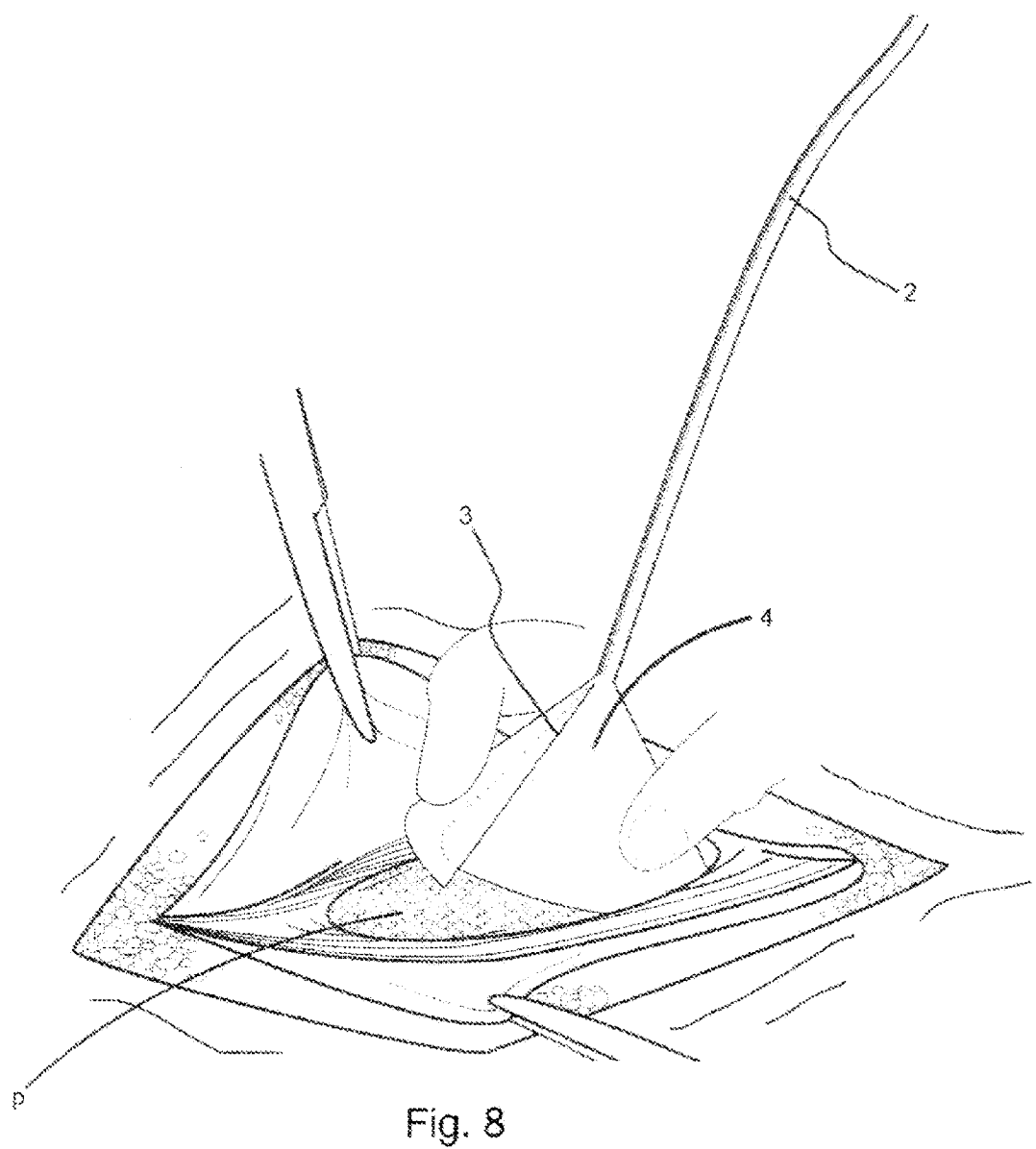
FIG. 8 illustrates in a top perspective view, the removal of the delivery device as it is removed from the prosthesis and retracted through the muscle wall defect.
Figure 9:
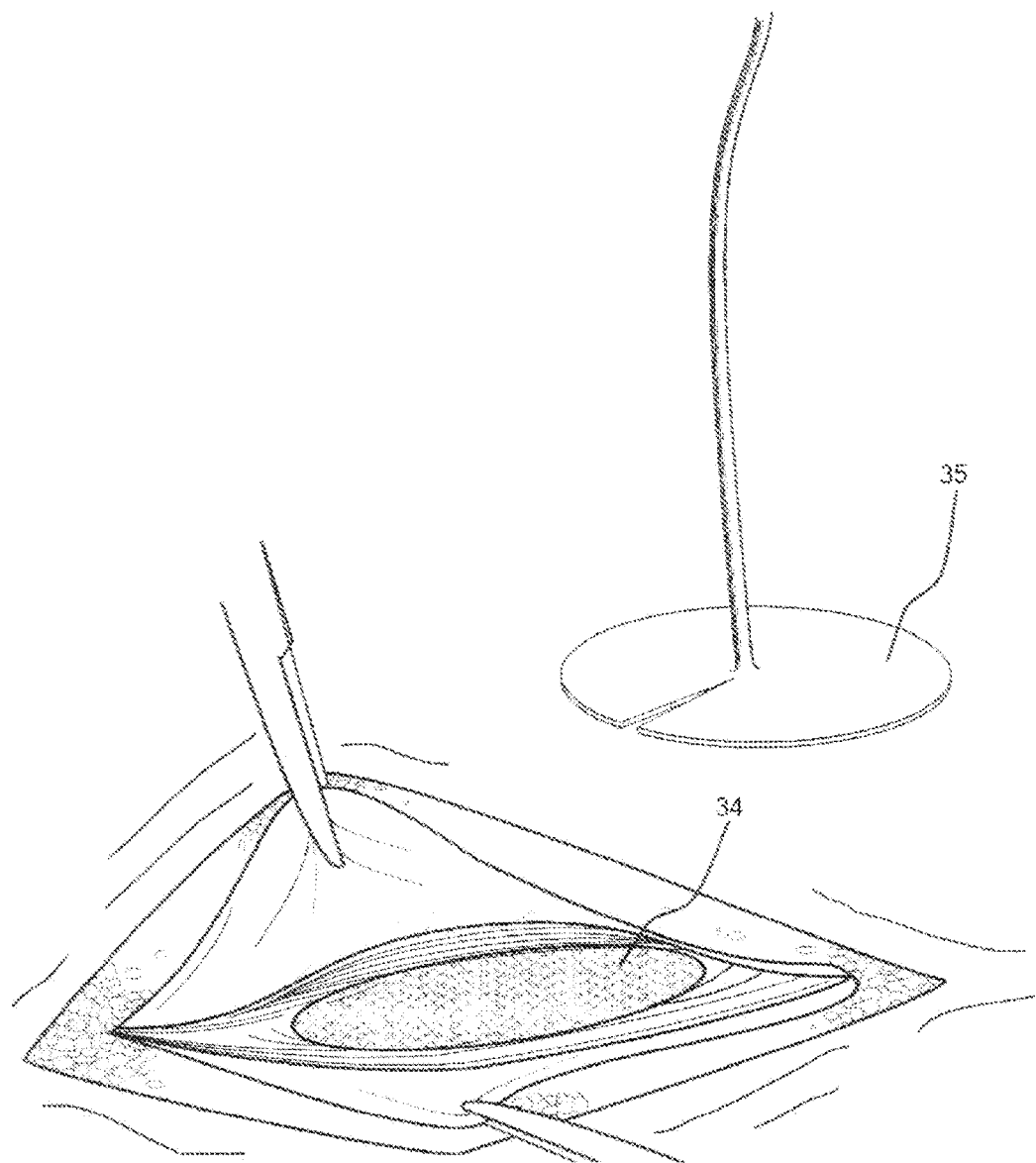
FIG. 9 illustrates in a top perspective view, the prosthesis that has been positioned and fixed in place, covering the muscle wall defect after removal of the delivery device.

After the prosthesis has been fixed to the muscle wall, the platen 4 can be removed from the pocket 11 of the prosthesis and retracted through the muscle wall defect by pulling on the handle 2, and forcing the platen, 4, into its collapsed position, as seen in FIG. 8. FIG. 9 shows the defect after the device, 1, has been removed, leaving behind only the prosthesis, P, which has now been fixed to the posterior side of the abdominal wall, covering the muscle wall defect. Anterior layers of tissue and skin are subsequently closed and sutured together.

In another embodiment of prosthesis P, illustrated in FIG. 11, the prosthesis P has a first layer, 12, and a second layer, 13, which contains an opening in the form of a diametrical slit, 14. Layers 12 and 13 are connected at the peripheral edge using stitching, 15. If required, the side of layer 12 that faces the patients' organs (not shown) is covered in a substance that reduces the formation of adhesions of tissue or organs to the implantable prosthesis.

When using the alternative prosthesis of FIG. 11, the platen 4 of the delivery device can be folded and subsequently inserted through a slit, 14, in the second layer of material, 13, and between layers 13 and 14, before it is released and allowed to expand back into its natural planar orientation and nested between layers 12 and 13. Thereafter, the prosthesis may be inserted and manipulated as described above.

Figure 10:
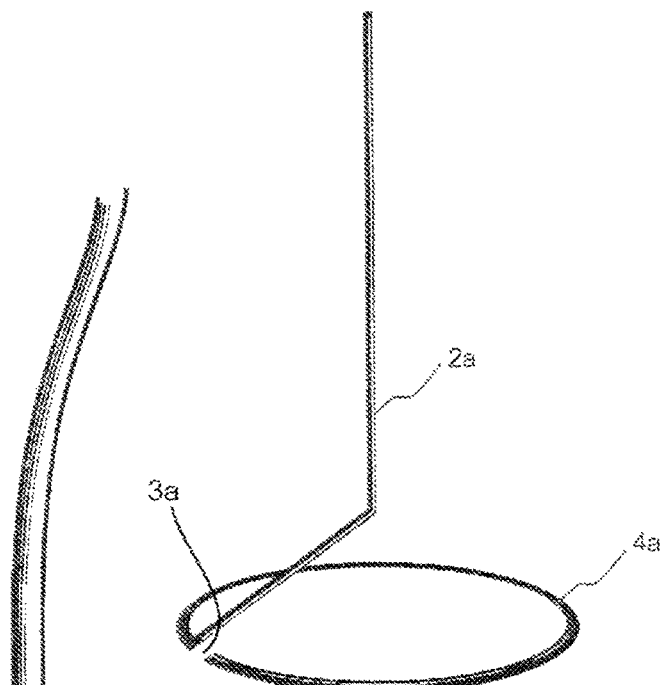
FIG. 10 depicts from a top perspective view, a second exemplary embodiment of the delivery device.

A second example embodiment of the delivery device is shown in FIG. 10, in which the support piece 4 is formed as a flexible removable ring, 4a, with a discontinuity, 3a, along its periphery to facilitate flexure. The ring 4a is connected to a radial extension of a handle, 2a to form an integral delivery device. The ring, 4a, could be, for example, constructed from a flexible material such as a metal, typically nitinol, or silicone. The ring, 4a, is therefore flexible and can be deformed to fit within the pocket, 11a, of the prosthesis P, through the slit, 14. The handle 2a has sufficient rigidity to manipulate the prosthesis P, once placed within the abdominal cavity.

Figure 12:
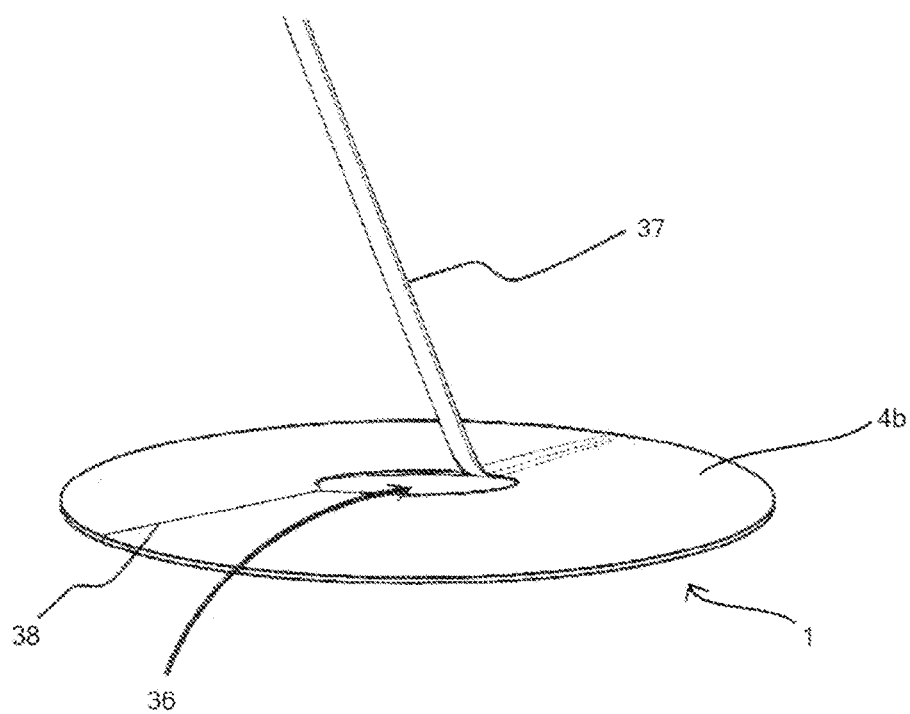
FIG. 12 depicts from a top perspective view, a third embodiment of the delivery device.
Figure 13:
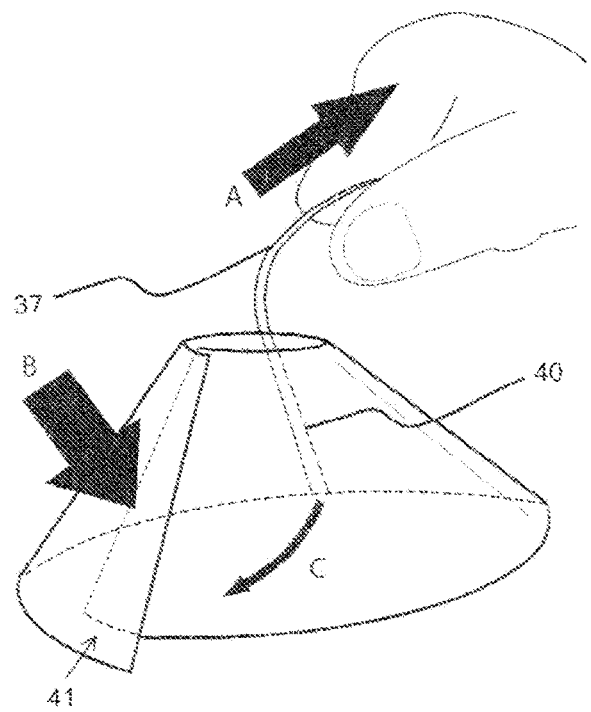
FIG. 13 illustrates in a top perspective view, the delivery device of FIG. 12 during removal thereof.

An alternative delivery device 1, as shown in FIGS. 12 and 13, has a support piece formed as an annular disc 4b with a radial slit 38. A central hole 36 is provided with a handle in the form of a flexible strap 37 secured to the periphery of the hole 36 diametrically opposed to the slit 38. The strap 37 has sufficient rigidity to control movement of the disc 4b but flexible enough to be accommodated in the hands of the surgeon. The device 1 is deployed as described above to position the prosthesis P. Once the prosthesis P is fixed, the device 1 can be urged into its collapsed position by pulling in direction, A, on the strap, 37, that is attached to the disc, 4b. This urges the disc 4b in to engagement with the overlying muscle wall and in to a conical shape, with the edges of the disc, 4b, on opposite sides of the slit 38 sliding over one another, as denoted by arrows B and C. This causes the two sides of the slit in the removable piece to overlap, as indicated at 41 into a collapsed configuration, and allows the support piece to be removed out of the prosthesis P and retracted through the muscle wall.

Figure 14:
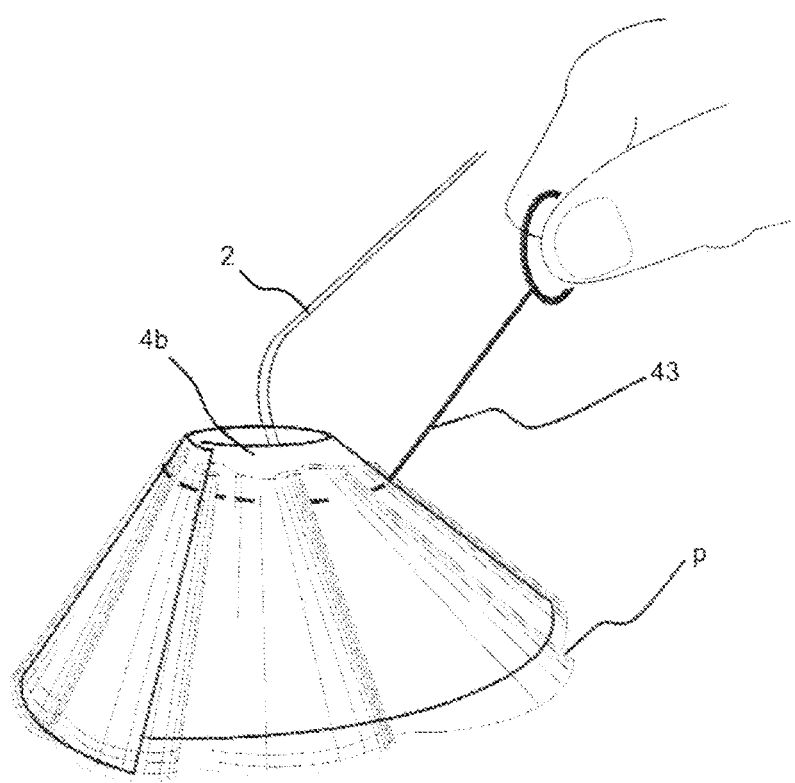
FIG. 14 illustrates in a top perspective view, the delivery device of FIG. 13 that is being urged its collapsed conformation using a prosthesis that has been fitted with a drawstring.

Another example embodiment of the delivery device is shown in FIG. 14, where the disc, 4b, is urged into, and/or retained in a collapsed conformation using a prosthesis, P, that has been fitted with a draw string 43 around an inner periphery of the pocket 11. The drawstring 43 is used to hold the disc 4b in a collapsed condition as it is inserted in to the body cavity, and then released to allow the disc to attain its planar condition. In the above embodiments, the prosthesis P has been formed from two layers of material joined at the periphery.

It will be appreciated that the juxtaposed layers of material defining the pocket 11 may be connected by adhesive in place of the stitching 10, or from a single piece of material with the layer 8 formed by folding the periphery of the piece over a former and tucks or pleats used to conform the layer to a reduced radius at its inner edge.

As a further alternative, the prostheses may be knitted to form the pocket 11 as a unitary component.

Figure 15:
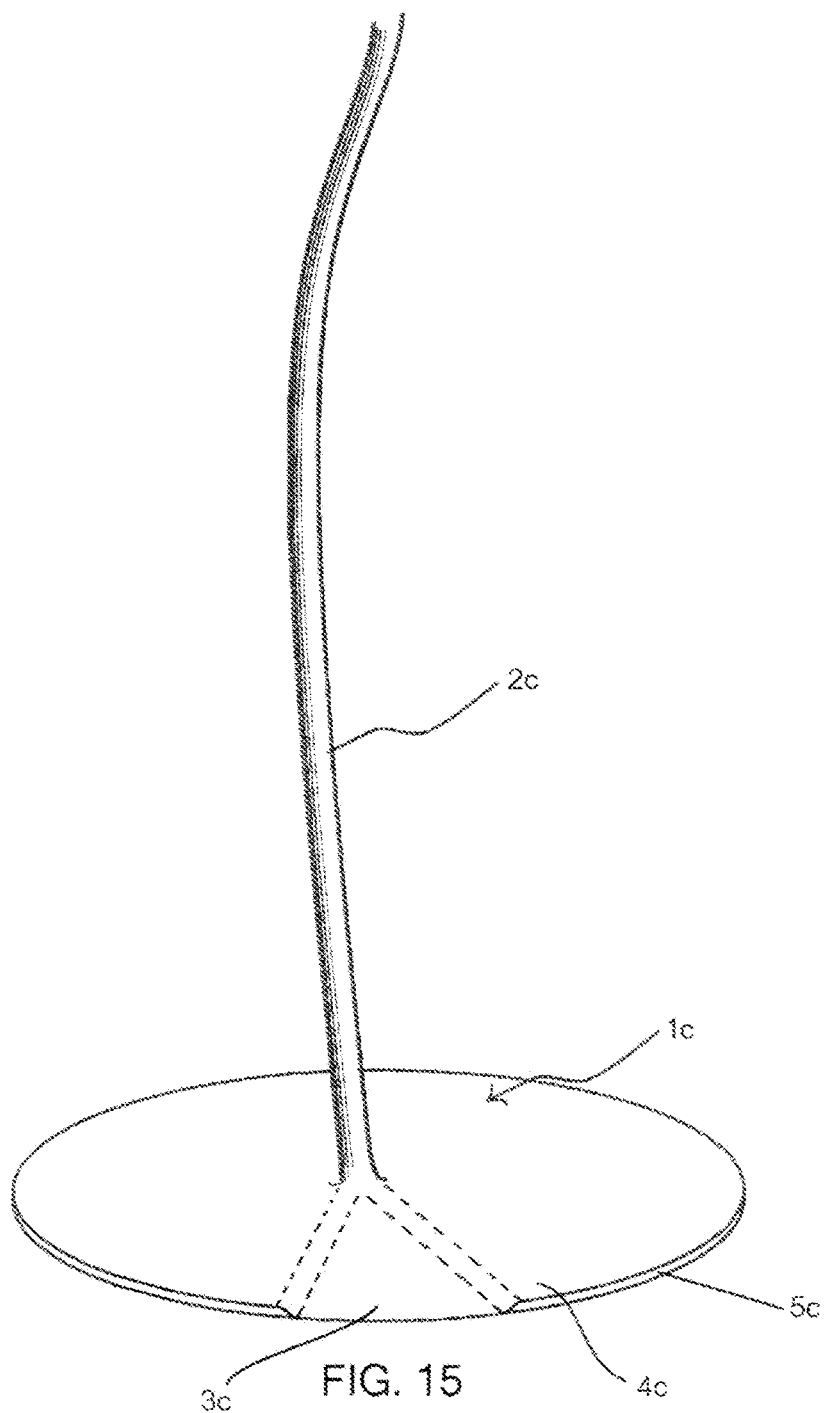
FIG. 15 is a view similar to FIG. 1, of a further embodiment of delivery device.

A further embodiment of delivery device 1c is shown in FIG. 15 where the platen, 4c, attached to handle 2e, is formed with a zone of weakness, indicated at 3c, where the thickness of the platen is reduced to provide a flexible web. The zone 3c extends about the peripheral edge 5c sufficiently to allow the platen 4c to adopt a collapsed configuration for insertion in the pocket. A continuous surface is thus provided on the platen and avoids the exposed edges of the slit 3.

It can be seen in each of the above that the delivery device 1 used to urge the prosthesis in the planar orientation is removed after use. This enables less foreign body material to be implanted, leading to less inflammation, less of a foreign body response, and a stronger, more flexible repair. The flexibility and physiological function of the abdominal wall are also better preserved. Because no support members or washers are left behind, the prosthesis can better conform to the moving contours of the patient's abdominal wall. In addition, because the surgeon can completely rely on the more rigid planar portion of the delivery device, the removable piece, to urge the prosthesis in the planar orientation, lighter-weight, and more biocompatible materials are be used to construct the prosthesis. These lighter-weight materials would be too flimsy and more difficult to handle if used in combination with the more slender support rings used in other inventions.

The invention claimed is:

1. A medical device for the repair and reinforcement of a muscle wall defect, and that comprises, in combination:
    (a) a biologically compatible implantable prosthesis having a first layer of material with a peripheral outer edge, and a second layer of material juxtaposed with said first layer and, connected to the first layer at said peripheral outer edge to provide a pocket between said layers; one of said layers of material containing an opening to allow access to said pocket between the first and second layers; and
    (b) a delivery device for delivering the prosthesis to a repair site, said delivery device having a generally planar support piece with a stable, self-supporting free body configuration to permit said support piece to be nested within the pocket between the first and second layer of the prosthesis, said support piece, in its free body configuration having a top surface, a bottom surface and an outer peripheral edge, said top surface being a continuous planar surface over a substantive portion of said support piece, said support piece including a single zone of weakness to facilitate deformation of said support piece, said support piece having flexibility sufficient to adopt a collapsed configuration allowing the support piece to pass through said opening, and the delivery device further comprising a handle extending from said continuous planar surface and connected to the support piece to transmit a force thereto, said handle having sufficient rigidity to transfer a bending moment to said support piece and move said support piece to said collapsed configuration to facilitate removal of the support piece from the implantable prosthesis after the implantable prosthesis has been positioned relative to the muscle defect, wherein said zone of weakness includes a single slit extending from said top surface through said bottom surface and through said outer peripheral edge, wherein a first portion of said support piece is on one side of said slit and a second portion of said support piece is on an opposite side of said slit, an edge of said first portion substantially abuts an edge of said second portion when said support piece is in said stable, self-supporting free body configuration.

2. A device of claim 1 wherein said handle is self-supporting and has sufficient rigidity to manipulate said support piece to position said prosthesis relative to said defect.

3. A device according to claim 1, wherein said pocket is dimensioned relative to said support piece so that said second layer overlies said continuous surface and said pocket permits insertion of a retainer through said second layer to secure said second layer to the muscle wall.

4. A device according to claim 3, wherein said second layer of the implantable prosthesis is formed as an annulus having a centrally located hole.

5. A device according to claim 3, wherein the opening in the second layer of material is a slit extending across at least a portion of the second layer.

6. A device according to claim 1, wherein said layers are connected by stitching about said outer peripheral edge.

7. A device according to claim 1 wherein said first layer and second layer are formed from a common material with a fold at said peripheral edge to connect said first layer and said second layer.

8. A device according to claim 1 wherein said first layer and second layer are integrally formed.

9. A device according to claim 1, wherein the implantable prosthesis is at least in part constructed using a biocompatible material that includes a plurality of interstices that are constructed and arranged to allow tissue in-growth.

10. A device according to claim 1, wherein a first portion of said support piece is on one side of said slit and a second portion of said support piece is on an opposite side of said slit, an edge of said first portion substantially abuts an edge of said second portion when said support piece is in said stable, self-supporting free body configuration.

11. A device according to claim 10, wherein said collapsed configuration of said support piece is cone-shaped.

12. A device according to claim 1, wherein said slit extends radially from adjacent said handle to said outer peripheral edge.

13. A device according to claim 1, wherein the support piece is at least in part comprised of a biologically compatible polymer material.

14. A device according to claim 1, wherein the support piece includes an inner region within the outer peripheral edge; the handle extending from the inner region.

15. A device according to claim 14, wherein the handle is flexible.

16. A device according to claim 1, wherein said handle is dimensioned to extend through the tissue or muscle wall defect when the implantable prosthesis and support piece are positioned beneath the defect.

17. A device according to claim 1, wherein said handle is attached to the support piece at a location that is diametrically opposed to said slit.

18. A device according to claim 1, wherein the prosthesis includes a retainer to maintain the support piece in its collapsed conformation.

19. A delivery device according to claim 18, wherein the prosthesis includes a draw string to maintain said support piece in a collapsed conformation.

20. A delivery device for delivering a prosthesis to a repair site, said delivery device having a generally planar support piece with a stable, self-supporting free body configuration to permit said support piece to be nested within a pocket between first and second layers of the prosthesis, said support piece, in its free body configuration having a top surface, a bottom surface and an outer peripheral edge, said top surface being a continuous planar surface over a substantive portion of said support piece, said support piece including a single zone of weakness disrupting said continuous planar surface to facilitate deformation of said support member, said support piece having flexibility sufficient to adopt a collapsed configuration allowing the support to pass through said opening, and the delivery device further comprising a handle that is connected to said top surface of the support piece to transmit a force thereto, said handle having sufficient rigidity to transfer a bending moment to said support piece and move said support piece to said collapsed configuration to facilitate removal of the support piece from the implantable prosthesis after the implantable prosthesis has been positioned relative to the muscle defect, wherein said zone of weakness includes a slit extending from said top surface through said bottom surface and through said outer peripheral edge, wherein a first portion of said support piece is on one side of said slit and a second portion of said support piece is on an opposite side of said slit, an edge of said first portion substantially abuts an edge of said second portion when said support piece is in said stable, self-supporting free body configuration.

21. A device according to claim 20 wherein said zone of weakness allows at least one portion of the support piece to overlap at least one other portion of the support piece.

22. A device according to claim 20, wherein said slit extends from adjacent said handle to said outer peripheral edge.

23. A delivery device according to claim 20, wherein the support piece is made from a biologically compatible material.

24. A delivery device according to claim 20, wherein the support piece includes an inner region within the outer peripheral edge and the handle extends from the inner region.

25. A delivery device according to claim 20, wherein said handle is self-supporting and is dimensioned to extend through the tissue or muscle wall defect when the implantable prosthesis and removable piece are positioned deep to the defect.

26. A delivery device according to claim 20, wherein a handle is attached to the support piece at a location that is diametrically opposed to said slit.

27. A delivery device for delivering a prosthesis to a repair site, said delivery device having a generally planar support piece with a stable, self-supporting free body configuration to permit said support piece to be nested within a pocket between first and second layers of the prosthesis, said support piece, in its free body configuration having a top surface and a bottom surface, said top surface being a continuous planar surface over a substantive portion of said support piece, said support piece having flexibility sufficient to adopt a collapsed configuration with a reduced circumference, the collapsed configuration being in the form of a cone with a single region of overlapped portions of the support piece, said overlapped portions including first and second portions of said support piece, an edge of said first portion substantially abuts an edge of said second portion when said support piece is in said stable, self-supporting free body configuration, the delivery device further comprising a handle that is connected to said top surface of said support piece to transmit a force thereto, and move said support piece to said collapsed configuration and facilitate removal of the support piece from the implantable prosthesis after the implantable prosthesis has been positioned relative to the muscle defect, said handle being self-supporting and having sufficient rigidity to manipulate said support piece to position said prosthesis relative to said defect, said handle being dimensioned to extend through the tissue or muscle wall defect when the implantable prosthesis and removable piece are positioned beneath the defect.

28. A delivery device according to claim 27, wherein said support piece has a continuous surface with a zone of weakness to facilitate movement of said support piece to said collapsed condition, said handle having sufficient rigidity to impart to said support piece a force to initiate movement to said collapsed condition.

29. A delivery device according to claim 28, wherein said zone of weakness includes a discontinuity in said continuous surface.

30. A delivery device according to claim 29, wherein said discontinuity is a radial slit extending from said handle.

* * * * *